USO11559211B2

(12) United States Patent
Jeong et al.

(10) Patent No.: US 11,559,211 B2
(45) Date of Patent: Jan. 24, 2023

(54) ELECTRONIC DEVICE FOR PROVIDING HEALTH INFORMATION BASED ON BIOMETRIC DATA, AND CONTROL METHOD THEREFOR

(71) Applicant: Samsung Electronics Co., Ltd., Suwon-si (KR)

(72) Inventors: Injo Jeong, Suwon-si (KR); Hyunguk Yoo, Suwon-si (KR); Kunkook Park, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 90 days.

(21) Appl. No.: 16/969,939

(22) PCT Filed: Feb. 13, 2019

(86) PCT No.: PCT/KR2019/001745
§ 371 (c)(1),
(2) Date: Aug. 13, 2020

(87) PCT Pub. No.: WO2019/160318
PCT Pub. Date: Aug. 22, 2019

(65) Prior Publication Data
US 2020/0405158 A1 Dec. 31, 2020

(30) Foreign Application Priority Data
Feb. 13, 2018 (KR) .................. 10-2018-0017833

(51) Int. Cl.
*A61B 5/0205* (2006.01)
*G16H 20/30* (2018.01)
(Continued)

(52) U.S. Cl.
CPC .......... *A61B 5/0205* (2013.01); *A61B 5/0533* (2013.01); *A61B 5/1118* (2013.01);
(Continued)

(58) Field of Classification Search
CPC ... A61B 5/0205; A61B 5/0533; A61B 5/1118;
A61B 5/1123; A61B 5/14546;
(Continued)

(56) References Cited

U.S. PATENT DOCUMENTS

2006/0016698 A1 1/2006 Lee et al.
2007/0028996 A1 2/2007 Quigley
(Continued)

FOREIGN PATENT DOCUMENTS

CN 105615881 A * 6/2016
JP 2016-116743 A 6/2016
(Continued)

OTHER PUBLICATIONS

International Search Report dated Jun. 11, 2019 in connection with International Patent Application No. PCT/KR2019/001745, 3 pages.
(Continued)

*Primary Examiner* — Joseph M Dietrich
*Assistant Examiner* — Michael T. Holtzclaw

(57) ABSTRACT

Disclosed is an electronic device comprising a processor and at least one sensor circuit comprising at least a biometric sensor and a fatigue sensor. The processor may be configured so as to detect biometric data of an external object by means of the biometric sensor, detect fatigue data of the external object by means of the fatigue sensor if the biometric data exceeds a designated second range, and output, by means of a designated external device, a fatigue notification indicating a fatigued state if the fatigue data exceeds a designated third range. Other various embodiments identified in the description are possible.

11 Claims, 12 Drawing Sheets

(51) Int. Cl.

| | |
|---|---|
| *G16H 50/30* | (2018.01) |
| *A61B 5/0533* | (2021.01) |
| *A61B 5/11* | (2006.01) |
| *A61B 5/00* | (2006.01) |
| *A61B 5/024* | (2006.01) |
| *G16H 40/67* | (2018.01) |
| *G16H 10/60* | (2018.01) |
| *A61B 5/318* | (2021.01) |
| *A61B 5/145* | (2006.01) |
| *A61B 5/1468* | (2006.01) |

(52) U.S. Cl.
CPC .......... *A61B 5/1123* (2013.01); *A61B 5/1468* (2013.01); *A61B 5/14546* (2013.01); *A61B 5/318* (2021.01); *A61B 5/742* (2013.01); *G16H 10/60* (2018.01); *G16H 20/30* (2018.01); *G16H 40/67* (2018.01); *G16H 50/30* (2018.01); *A61B 5/02416* (2013.01); *A61B 2560/0257* (2013.01); *A61B 2562/0219* (2013.01)

(58) Field of Classification Search
CPC ....... A61B 5/1468; A61B 5/318; A61B 5/742; A61B 5/02416; A61B 2560/0257; A61B 2562/0219; A61B 2503/10; A61B 5/0531; A61B 5/14517; A61B 5/1477; A61B 5/681; A61B 5/4884; A61B 5/11; A61B 5/746; A61B 5/4866; A61B 5/02438; G16H 10/60; G16H 20/30; G16H 40/67; G16H 50/30
See application file for complete search history.

(56) References Cited

U.S. PATENT DOCUMENTS

| | | | | |
|---|---|---|---|---|
| 2007/0219059 A1* | 9/2007 | Schwartz | ........... | A61B 5/02405 |
| | | | | 482/8 |
| 2010/0137748 A1* | 6/2010 | Sone | ...... | A61B 5/681 |
| | | | | 600/595 |
| 2015/0051721 A1* | 2/2015 | Cheng | ......... | G06K 9/0055 |
| | | | | 434/247 |
| 2015/0186609 A1* | 7/2015 | Utter, II | ......... | A61B 5/742 |
| | | | | 600/301 |
| 2016/0027324 A1* | 1/2016 | Wisbey | ......... | G16H 40/63 |
| | | | | 434/247 |
| 2016/0071393 A1* | 3/2016 | Kaplan | ......... | A61B 5/162 |
| | | | | 340/539.12 |
| 2016/0143579 A1* | 5/2016 | Martikka | ......... | A61B 5/0205 |
| | | | | 600/301 |
| 2016/0157743 A1* | 6/2016 | Bounyong | ......... | A61B 5/389 |
| | | | | 600/301 |
| 2016/0317074 A1 | 11/2016 | Kawai et al. | | |
| 2016/0317099 A1 | 11/2016 | Kawai et al. | | |
| 2016/0328524 A1 | 11/2016 | Kawai et al. | | |
| 2016/0328533 A1 | 11/2016 | Kawai et al. | | |
| 2016/0344808 A1 | 11/2016 | Smith et al. | | |
| 2016/0345865 A1* | 12/2016 | Agrawal | ......... | A61B 5/0022 |
| 2017/0035314 A1 | 2/2017 | Kronstedt et al. | | |
| 2017/0188894 A1* | 7/2017 | Chang | ......... | A61B 5/1121 |
| 2017/0228996 A1* | 8/2017 | Theytaz | ......... | G16H 20/30 |
| 2018/0207480 A1 | 7/2018 | Hong | | |
| 2018/0263539 A1* | 9/2018 | Javey | ......... | A61B 5/1477 |
| 2019/0046107 A1* | 2/2019 | Jang | ......... | A61B 5/4519 |
| 2019/0183412 A1* | 6/2019 | Huijbregts | ......... | A61B 5/165 |
| 2019/0183430 A1* | 6/2019 | Alphonse | ......... | A61B 5/1118 |
| 2019/0290181 A1* | 9/2019 | Mrvaljevic | ......... | A61B 5/00 |
| 2019/0374124 A1 | 12/2019 | Kronstedt et al. | | |
| 2020/0146567 A1* | 5/2020 | Dennis | ......... | A61B 5/7275 |
| 2020/0285873 A1* | 9/2020 | Condon | ......... | G06K 9/00523 |

FOREIGN PATENT DOCUMENTS

| | | |
|---|---|---|
| KR | 10-2007-0028996 A | 3/2007 |
| KR | 10-2007-0089906 A | 9/2007 |
| KR | 10-1044883 B1 | 6/2011 |
| KR | 10-1141523 B1 | 5/2012 |
| KR | 10-2015-0095439 A | 8/2015 |
| KR | 10-2017-0007690 A | 1/2017 |
| KR | 10-2017-0060514 A | 6/2017 |
| WO | 2015/107710 A1 | 7/2015 |
| WO | WO-2016007944 A2 * | 1/2016 ......... A61B 10/0064 |

OTHER PUBLICATIONS

Korean Intellectual Property Office, "Request for the Submission of an Opinion," dated Aug. 30, 2022, in connection with Korean Patent Application No. 10-2018-0017833, 10 pages.

\* cited by examiner

ELECTRONIC DEVICE FOR PROVIDING HEALTH INFORMATION BASED ON BIOMETRIC DATA, AND CONTROL METHOD THEREFOR

CROSS-REFERENCE TO RELATED APPLICATIONS

This application is a 371 of International Application No. PCT/KR2019/001745 filed on Feb. 13, 2019, which claims priority to Korean Patent Application No. 10-2018-0017833 filed on Feb. 13, 2018, the disclosures of which are herein incorporated by reference in their entirety.

1. FIELD

Various embodiments disclosed in the present disclosure relate to an electronic device for health care based on biometric information, and a control method for the electronic device.

2. DESCRIPTION OF RELATED ART

More and more people are going on a diet for fitness or health care. However, a diet based on an extreme regimen for weight loss may not only put strain on the body, but also cause the yo-yo effect. Therefore, for a sustainable diet, exercise needs to be combined with diet management. In this case, excessive exercise may also put strain on the body. For example, excessive exercise may cause joint and muscle injury.

In the related art, an electronic device (e.g., a smartphone) may provide information for assisting a user's exercise. For example, the electronic device may provide information related to the number of steps, the heart rate, the exercise time, the exercise type, sleep, stress, food, and the like. Further, the electronic device may provide the amount of calories burned and the like using information input by the user and measured information. The electronic device according to the related art generally provides estimated information based on information with low accuracy, and thus it is likely to provide inaccurate information to the user.

SUMMARY

An electronic device according to an embodiment of the present disclosure may comprise at least one sensor circuit including at least a biometric sensor and a fatigue sensor, and a processor, wherein the processor may be configured to sense biometric information of an external object using the biometric sensor, sense fatigue information of the external object using the fatigue sensor if the biometric information is equal to or greater than a specified second range, and output a fatigue notification indicating a fatigue state using a specified external device if the fatigue information is equal to or greater than a specified third range.

Furthermore, a method of providing a fatigue notification by an electronic device according to an embodiment of the present disclosure may comprise sensing biometric information of an external object using a biometric sensor, sensing fatigue information of the external object using a fatigue sensor if the biometric information is equal to or greater than a specified second range, and outputting a fatigue notification indicating a fatigue state using a specified external device if the fatigue information is equal to or greater than a specified third range.

According to various embodiments disclosed in the present disclosure, it is possible to reduce an injury risk while maximizing an exercise effect.

In addition, according to various embodiments, it is possible to maintain a user's willpower to diet by providing information for sufficient rest.

Besides, various effects may be provided that are directly or indirectly identified through the present disclosure.

BRIEF DESCRIPTION OF THE DRAWINGS

With respect to the description of the drawings, the same or similar reference signs may be used for the same or similar elements.

DETAILED DESCRIPTION

Figure 1:
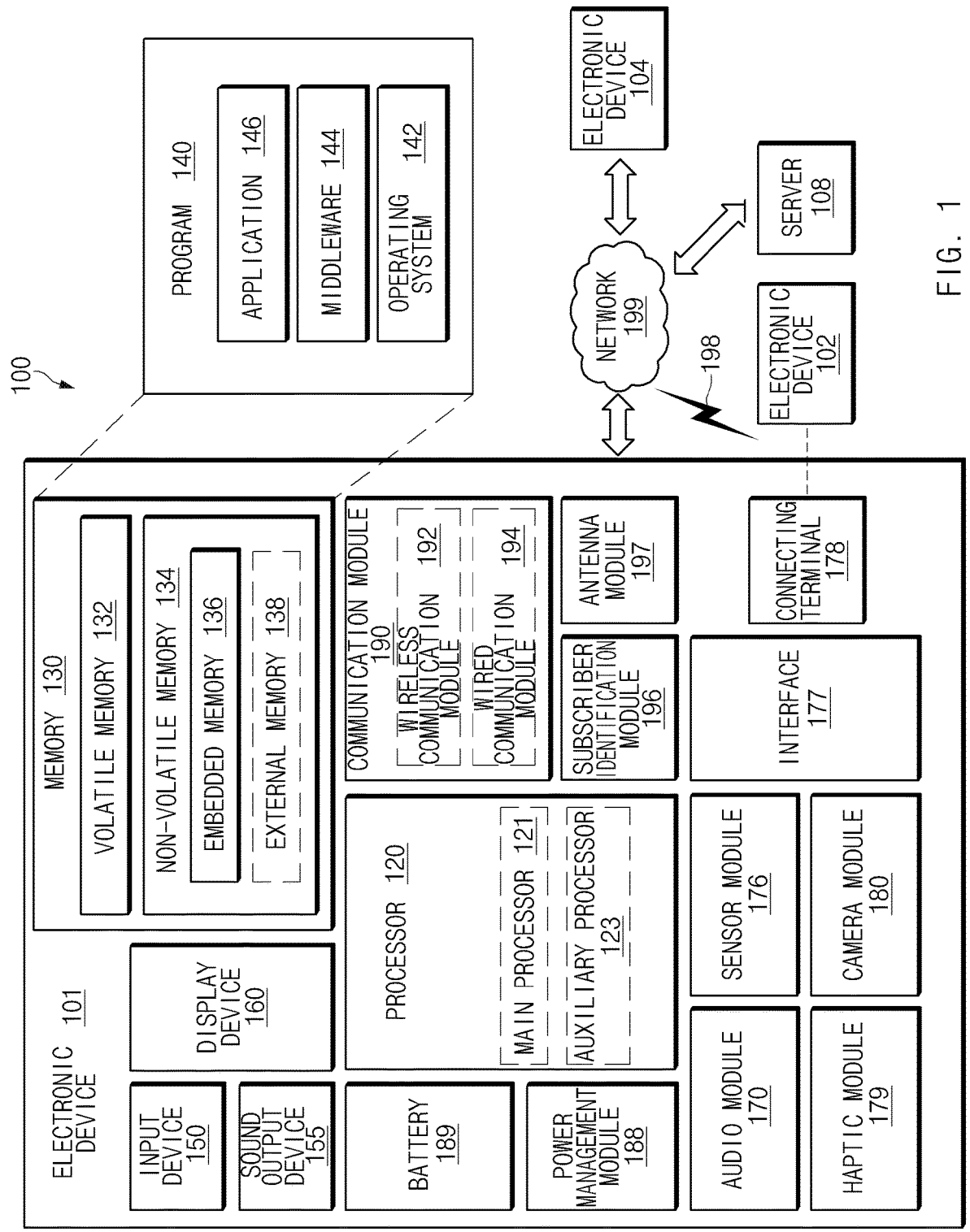
FIG. 1 is a block diagram illustrating an electronic device in a network environment for providing health information based on biometric information, according to various embodiments.

Hereinafter, various embodiments disclosed in the present disclosure will be described with reference to the accompanying drawings. It should be appreciated that embodiments and the terms used therein are not intended to limit the technologies set forth herein to particular embodiments and include various changes, equivalents, and/or replacements for a corresponding embodiment. With regard to the description of the drawings, similar reference numerals may be used to refer to similar elements. A singular form is intended to include a plural form, unless the context clearly indicates otherwise. As used here, the phrases "A or B", "at least one of A or/and B", or the like may include all possible combinations of the items listed together. The terms such as "first", "second", "the first", or "the second" may modify corresponding components, regardless of order and/or importance, and are used to distinguish one component from another, but do not limit the components. When a certain (e.g., first) component is referred to as being "(functionally or communicatively) coupled" or "connected" to another (e.g., the second) component, it is to be understood that the certain component may be directly connected to the other component, or may be connected through any other component (e.g., third component).

As used here, the phrase "configured to (or set to)" may be interchangeably used with "suitable for", "having a capacity to", "adapted to", "made to", "capable of" or "designed to" depending on circumstances, for example, in terms of hardware or software. In some circumstances, the phrase "device configured to" may mean that the device "can" perform an operation with other devices or parts. For example, the phrase "processor configured (or set) to perform A, B, and C" may mean a dedicated processor (e.g., embedded processor) for performing corresponding operations, or a generic-purpose processor (e.g., central processing unit (CPU) or application processor) that performs the operations by executing one or more software programs stored in a memory device.

An electronic device according to various embodiments of the present disclosure may include at least one of, for example, a smartphone, a tablet PC, a mobile phone, a video phone, an e-book reader, a desktop PC, a laptop PC, a netbook computer, a workstation, a server, a PDA, a portable multimedia player (PMP), an MP3 player, a medical device, a camera, or a wearable device. The wearable device may include at least one of an accessory-type device (e.g., watches, rings, bracelets, anklets, necklaces, glasses, contact lenses, or head-mounted devices (HMD), a textiles or clothing integrated-type device (e.g., electronic clothing), a body attachment-type device (e.g., skin pads or tattoo), or a bio-implantable-type circuit. In some embodiments, the electronic device may include at least one of, for example, a television, a digital video disk (DVD) player, an audio device, a refrigerator, an air conditioner, a cleaner, an oven, a microwave, a washing machine, an air purifier, a set-top box, a home automation control panel, a security control panel, a media box (e.g., Samsung HomeSync™, Apple TV™, or Google TV™), a game consoles (e.g., Xbox™, PlayStation™), an electronic dictionary, an electronic key, a camcorder, or a digital photo frame.

In another embodiment, the electronic device may include at least one of various medical devices (e.g., various portable medical measurement devices (such as a blood glucose meter, a heart rate monitor, a blood pressure meter, or a body temperature meter), magnetic resonance angiography (MRA), magnetic resonance imaging (MRI), computed tomography (CT), imaging device, a ultrasound machine, and the like, a navigation device, a global navigation satellite system (GNSS), an event data recorder (EDR), a flight data recorder (FDR), a vehicle infotainment device, an electronic device for a ship (e.g., a navigation device for a ship, a gyro-compass, and the like), avionics, a security device, an automotive head unit, a robot for home or industry, a drone, an automatic teller's machine (ATM) in banks, point of sales in a shop, or an Internet-of-things device (a light bulb, various sensors, a sprinkler device, a fire alarm, a thermostat, a streetlamp, a toaster, a sporting goods, a hot water tank, a heater, a boiler, and the like). According to some embodiments, the electronic device may include at least one of a part of furniture, a building/structure, or a vehicle, an electronic board, an electronic signature receiving device, a projector, or various measuring devices (e.g., a water meter, an electric meter, a gas meter, or radio wave meter, and the like). In various embodiments, the electronic device may be flexible or a combination of two or more of the various devices described above. According to an embodiment of the disclosure, the electronic devices are not limited to those described above. In the present disclosure, the term user may refer to a person using an electronic device or a device using the electronic device (e.g., an artificial intelligence electronic device).

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Operations of the various electronic devices 101 described below may be performed by the processor 120. For example, the processor 120 may control operations of the electronic device 101 based on instructions stored in the memory 130.

Figure 2:
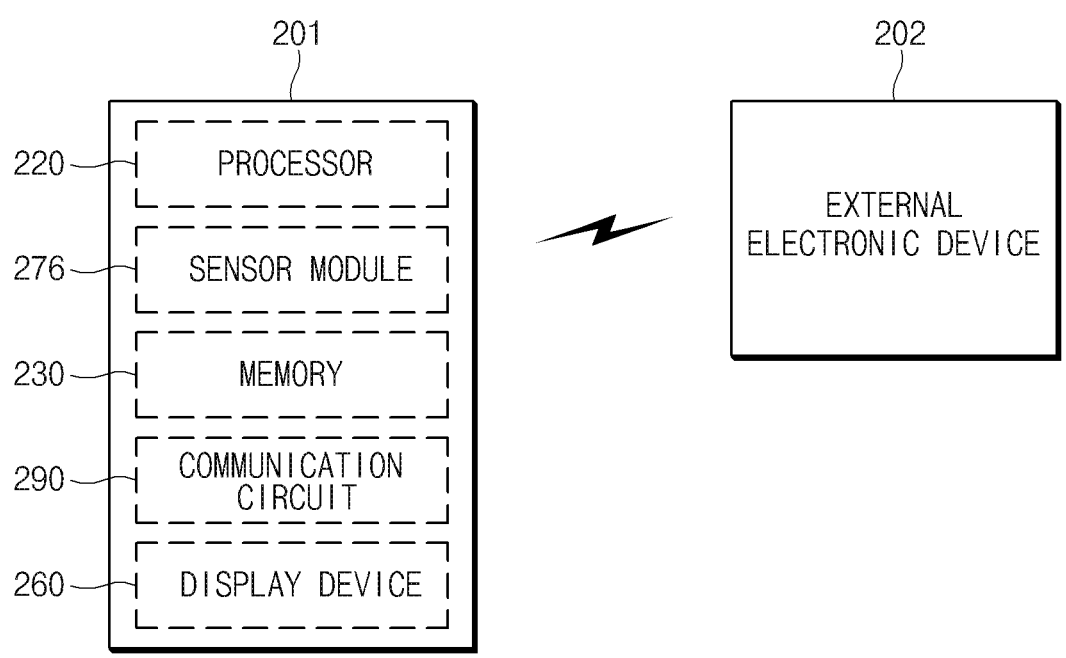
FIG. 2 is a block diagram illustrating the electronic device according to various embodiments.

FIG. 2 is a block diagram illustrating the electronic device according to various embodiments.

Referring to FIG. 2, according to an embodiment, an electronic device 201 (e.g., the electronic device 101 of FIG. 1) may include at least one of a processor 220 (e.g., the processor 120 of FIG. 1), a memory 230 (e.g., the memory 130 of FIG. 1), a sensor module 276 (e.g., the sensor module 176 of FIG. 1), a communication circuit 290 (e.g., the communication module 190 of FIG. 1), or a display device 260 (e.g., the display device 160 of FIG. 1).

According to an embodiment, the processor 220 may be operably connected to at least one of the memory 230, the sensor module 276, the communication circuit 290, or the display device 260 to control operations of the electronic device 201 and/or the components of the electronic device 201.

According to an embodiment, the memory 230 may be operably connected to the processor 220 to store instructions for controlling the processor 220. According to an embodiment, the memory 230 may store instructions that cause the processor 220 to perform operations of the processor 220 or the electronic device 201 described below.

According to an embodiment, the memory 230 may store biometric information measured by the sensor module 276. According to another embodiment, the memory 230 may store reference values (e.g., a reference table) for comparison with the biometric information. For example, the memory 230 may store a table showing a relationship of lactic acid concentration or a fatigue level to the amount of charge. For another example, the memory 230 may store a table showing the relationship of glucose concentration or blood glucose to the amount of charge.

According to an embodiment, the memory 230 may store user profile information, initial setting information, and so on. For example, the memory 230 may store measured values associated with a user profile. The user profile information may be generated based on a user input or may be received from an external electronic device 202. For example, the user profile information may include a user name, ID, age, date of birth, height, and/or weight.

According to an embodiment, the communication circuit 290 may provide wired or wireless communication with the external electronic device 202 (e.g., an electronic device including a display such as a smartphone) through a network. For example, the communication circuit 290 may provide communication with the external electronic device 202 using short-range wireless communication (e.g., at least one of near field communication (NFC), WiFi, Zigbee, Z-wave, Bluetooth, or Bluetooth low energy (BLE)). For another example, the communication circuit 290 may provide communication with the external electronic device 202 using wireless communication such as cellular communication. According to an embodiment, the communication circuit 290 may transmit information stored in the memory to the external electronic device 202 or receive information from the external electronic device 202, under the control of the processor 220.

According to various embodiments, the display device 260 may display the state, notification, and/or sensing information of the electronic device 201 according to the instruction of the processor 220. According to an embodiment, the display device 260 may include a plurality of light emitting diodes (LEDs). For example, the display device 260 may display the power state of the electronic device 201, the sensing mode of the electronic device 201, and/or notification information using the blinking of the LED, the color of the LED, and/or the number of lit LEDs.

The sensor module 276 may include a plurality of electrodes capable of measuring a plurality of kinds of biometric information and/or environmental information. According to an embodiment, the sensor module 276 may include an electrode capable of measuring at least one of a fatigue level, blood pressure, blood glucose, electrocardiogram, galvanic skin reflex (GSR), grip, or skin temperature. The sensor module 276 may include at least one electrode and may include a pad capable of contacting a user's skin, or may be connected to a detachable pad. For another example, the sensor module 276 may be connected to a detachable patch pad. According to another embodiment, the sensor module 276 may further include at least one sensor (e.g., motion sensor) for sensing user information (e.g., movement). For example, the sensor module 276 may also include a photoplethysmography (PPG) sensor, a gyro sensor, a gas sensor, and/or an acceleration sensor. According to an embodiment, the sensor module 276 may further include at least one sensor for sensing information (e.g., air pressure, temperature, and/or humidity) associated with the environment of the electronic device 201.

According to an embodiment, the sensor module 276 may include at least one of a motion sensor for sensing physical movement of the electronic device 201, a biometric information sensor for measuring biometric information of an external object (e.g., a user) based on an electro-optical response, or a fatigue sensor for measuring a fatigue level of an external object based at least on a chemical reaction. For example, the motion sensor may include at least one of an acceleration sensor, a gyroscope, an altitude sensor, or an air pressure sensor. For example, the biometric information sensor may include at least one of a galvanic skin response (GSR) sensor, a PPG sensor, or an ECG sensor. For example, the fatigue sensor may include a plurality of electrodes capable of measuring lactic acid concentration based on a chemical reaction.

The configuration of the electronic device 201 illustrated in FIG. 2 is exemplary, and the configuration of the electronic device 201 is not limited thereto. For example, the electronic device 201 may not include at least one of the components illustrated in FIG. 2, or may further include at least one component not illustrated in FIG. 2. For example, the electronic device 201 may further include a user interface (e.g., at least one button) for receiving a user input and/or a battery. For another example, the electronic device 201 may further include a voltage application device (e.g., power management integrated circuit (PMIC)) capable of applying a voltage to the electrode, and/or a current/voltage measurement device. For yet another example, the electronic device 201 may include an analog-to-digital converter (ADC) or an analog front end (AFE) for receiving/modulating the analog signal received from the sensor module 276.

According to an embodiment, the electronic device 201 may include a user interface including at least one button. For example, the user interface may include a button for controlling a power supply of the electronic device 201 and a button for selecting a measurement mode. According to another embodiment, the electronic device 201 may receive a user input via a rotatable ring positioned around the display device 260. For example, the user may select the measurement mode by rotating the ring clockwise or counterclockwise. According to another embodiment, the electronic device 201 may receive a touch input from the display device 260. According to another embodiment, the electronic device 201 may receive a user input from the external electronic device 202.

According to an embodiment, the processor 220 may acquire at least one kind of biometric information using the sensor module 276 in response to the user input. For example, the processor 220 may receive raw data from the sensor module 276, and may acquire biometric information (e.g., heart rate information, blood glucose, a fatigue level, or the like) corresponding to the raw data using values stored in the memory 230. For example, the processor 220 may acquire the raw data by applying a specified voltage to the sensor module 276 and measuring the amount of charge using the sensor module 276. For another example, the processor 220 may acquire heart rate information based on a voltage difference or illuminance sensed by the sensor module 276.

According to an embodiment, the processor 220 may provide the acquired biometric information to the user. For example, the processor 220 may display the biometric information on the display device 260. For another example, the processor 220 may transmit the biometric information to the external electronic device 202 using the communication circuit 290. The external electronic device 202 may display the received biometric information on the display. For example, the biometric information may be displayed using numeric and/or graphical elements (e.g., graphs).

According to an embodiment, the processor 220 may provide a notification to the user if the acquired biometric information satisfies a specified condition. For example, the processor 201 may provide the notification using the display device 260 or other output means (e.g., voice or tactile output means) of the electronic device 201. For another example, the processor 201 may transmit notification information to the external electronic device 202, thereby making it possible to provide the notification using the external electronic device 202.

According to an embodiment, the processor 220 may determine a start of exercise and an exercise type. For example, the processor 220 may sense the movement of the electronic device 201 using the acceleration sensor and/or the gyro sensor included in the sensor module 276, and may determine the start of exercise if the detected movement is equal to or greater than a specified range. For example, the processor 220 may determine the exercise type using the acceleration sensor and/or the gyro sensor included in the sensor module 276. Examples of the exercise type may include walking, running, swimming, cycling, treadmill, rowing, and stamper.

According to an embodiment, the processor 220 may measure the heart rate information using the sensor module 276. For example, the processor 220 may measure the heart rate information if the start of exercise is sensed. For example, the processor 220 may acquire the heart rate information based on a voltage difference between at least two electrodes included in the sensor module 276 or based on the PPG sensor.

According to an embodiment, the processor 220 may measure the fatigue level using the sensor module 276. For example, the processor 220 may measure the fatigue level using two electrodes included in the sensor module 276. For example, a catalyst capable of facilitating the decomposition of lactic acid may be applied to the surface of one of two electrodes. The processor 220 may determine the lactic acid concentration by applying a voltage between two electrodes included in the sensor module 276 and measuring the amount of current flowing between the electrodes. For example, the processor 220 may determine the fatigue level by comparing the lactic acid concentration with a specified value in the memory 230.

According to an embodiment, the processor 220 may measure the fatigue level based on the heart rate information. For example, the processor 220 may measure the fatigue level if the heart rate is equal to or greater than a specified range. The specified range may be determined based on the maximum heart rate corresponding to the age of the user. For example, the processor 220 may acquire age of the user from the user profile stored in the memory 230 and may determine the specified range based on the maximum heart rate corresponding to the age of the user. The specified range may be less than about 70% of the maximum heart rate.

According to an embodiment, the processor 220 may provide a notification (e.g., recommending to stop exercise or rest) to the user if the fatigue level is equal to or greater than the specified first range. For example, the processor 220 may provide a visual, tactile, and/or audible notification using the display device 260 or other output means of the electronic device 201. For another example, the processor 220 may provide the notification via the external electronic device 202. It is possible to induce the user to rest by providing the notification to the user based on the fatigue level. By not overloading the user, it is possible to prevent injury to the user.

According to an embodiment, when the exercise is stopped (e.g., when resting), the processor 220 may continuously or periodically measure the heart rate information and/or a fatigue level. If the fatigue level is reduced to be less than the specified second range, the processor 220 may provide a notification to the user using the electronic device 201 or the external electronic device 202. For example, if the heart rate is less than the specified value and the fatigue level is reduced to be less than the specified second range, the processor 220 may provide a notification to the user. Efficient exercise may be continued by providing, to the user, the notification to recommend the exercise.

According to an embodiment, after the exercise is finished, the processor 220 may display calories burned through the display device 260. For example, the processor 220 may provide calories-burned information to the user using a linked application or the external electronic device 202. In addition, the processor 220 may provide information on the recommended exercise and an exercise time to the user using the linked application or the external electronic device 202.

According to various embodiments, the electronic device 201 may include at least one sensor circuit 276 including at least the biometric sensor and the fatigue sensor and a processor 220. The processor 220 may be configured to sense biometric information of an external object (e.g., user) using the biometric sensor, sense fatigue information of the external object using a fatigue sensor if the biometric information is equal to or greater than a specified second range, and output a fatigue notification indicating a fatigue state using the specified external device 202 if the fatigue information is equal to or greater than a specified third range.

According to an embodiment, the at least one sensor circuit 276 may further include the motion sensor. The processor 220 may be configured to sense the movement of the electronic device 201 using the motion sensor, and sense the biometric information if the movement is equal to or greater than a specified first range. For example, the motion sensor may include at least one of an acceleration sensor, a gyroscope, an air pressure sensor, or an altitude sensor.

According to an embodiment, the specified first range may be set based on at least one of the age, the gender, the genetic characteristics (e.g., deoxyribonucleic acid, DNA), or activity information of the specified user.

According to an embodiment, the processor 220 may be configured to identify the movement of the electronic device 201 using the motion sensor, and determine at least one of the exercise type or the exercise time if the movement of the identified electronic device is within a specified range.

According to an embodiment, the processor 220 may be configured to sense the biometric information of the external object if the exercise type is determined.

According to an embodiment, the processor 220 may be configured to calculate calories burned based on at least one of the exercise type or exercise time, and output the calculated calories burned using the specified external device 202.

According to an embodiment, the specified external device 202 may include a display device. The processor 220 may be configured to display the fatigue notification using the display device, and then display an exercise notification indicating an exercise using the display device of the specified external device 202 if the fatigue information of the external object is less than a specified fourth range.

According to an embodiment, the fatigue sensor may be configured to apply a specified voltage between a first electrode and a second electrode including a catalyst layer for reaction with lactic acid, measure an amount of current between the first electrode and the second electrode, measure the lactic acid concentration based on the amount of current amount, and sense the fatigue information based at least on the measured lactic acid concentration.

For example, the first electrode and the second electrode may be replaceable film type electrode modules.

According to an embodiment, the biometric sensor may include at least one of a photoplethysmography (PPG) sensor, an electrocardiography (ECG) sensor, or a galvanic skin response (GSR) sensor.

According to an embodiment, the external electronic device 202 may include the electronic device 201 or a configuration similar to the electronic device 101.

According to an embodiment, the electronic device 201 may be a device capable of adhering to or sticking to the user, or a wearable device. For example, the electronic device 201 may include a pad or patch adhesive to the user. For another example, the electronic device 201 may be a watch, an armband, a headband, a bracelet, an anklet, a chest band, or a waist strip. For another example, the electronic device 201 may be a kind of clothes. The electronic device 201 may be clothes having a part where at least a portion of the body may be in close contact with the body.

Referring to FIG. 2, the operations of the electronic device 201 have been mainly described for logical configurations of the electronic device 201. Hereinafter, referring to FIG. 3, physical configurations of the electronic device 201 according to an embodiment will be described.

Figure 3:
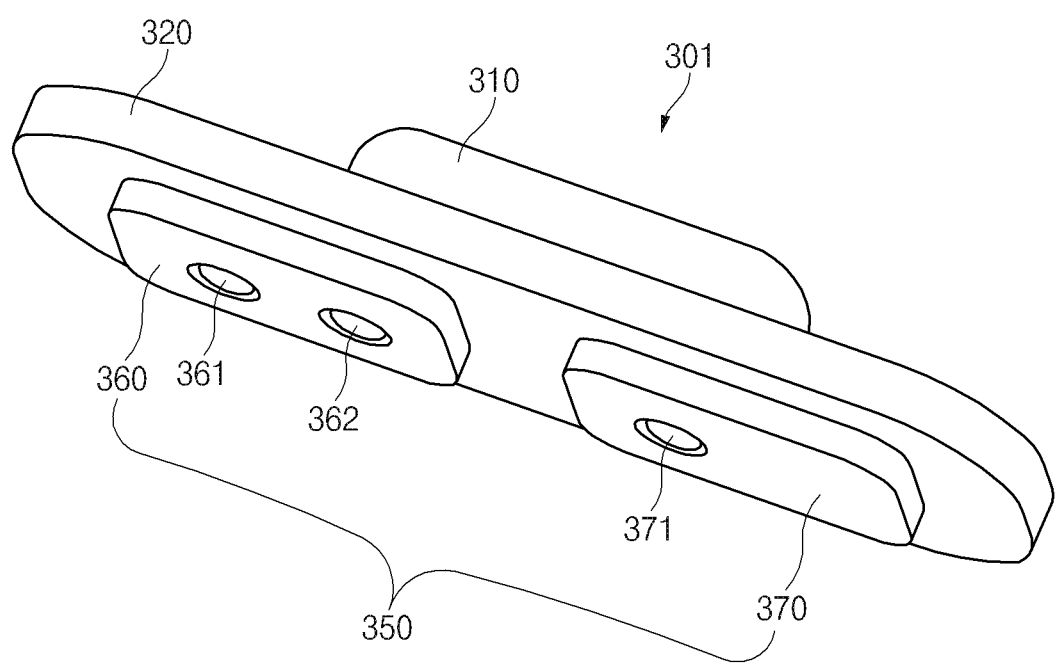
FIG. 3 is a schematic diagram illustrating the electronic device according to an embodiment.

FIG. 3 is a schematic diagram illustrating the electronic device according to an embodiment.

Referring to FIG. 3, an electronic device 301 according to an embodiment (e.g., the electronic device 201 of FIG. 2) may include at least one of an upper main body 310, a main body 320, or a lower pad 350.

According to an embodiment, the upper main body 310 may include a display device (e.g., the display device 260 of FIG. 2) and a user interface. The main body 320 is located under the upper main body 310 and may include various components of the electronic device 301 together with the upper main body 310. For example, the upper main body 310 and the main body 320 may include at least one of the display device 260, the communication circuit 290, the processor 220, the memory 230, or a battery. For example, the upper main body 310 and the main body 320 may a printed circuit board (PCB) on which at least one of the display device 260, the communication circuit (e.g., the communication circuit 290 of FIG. 2), the processor (e.g., the processor 220 of FIG. 2), or a memory (e.g., the memory 230 of FIG. 2), or at least one sensor (e.g., a motion sensor) is mounted.

According to an embodiment, the lower pad 350 (e.g., the sensor module 276) may be formed of a composite electrode in the form of a patch pad, which is located under the main body 320 and includes a plurality of pads. For example, the lower pad 350 may include a first pad 360 and a second pad 370. According to an embodiment, the lower pad 350 may be detachably coupled to the main body 320. For example, by changing at least one pad (e.g., the first pad 360 and/or the second pad 370), the type of biometric information that the electronic device 301 is able to sense may be changed. According to an embodiment, the lower pad 350 may include a plurality of pads. According to an embodiment, the lower pad 350 may include one or more patch pads.

According to an embodiment, the first pad 360 may include at least one of a first electrode 361 or a second electrode 362. For example, the second pad 370 may include a third electrode 371. The configurations of the first pad 360 and the second pad 370 are not limited to the shape in FIG. 3. For example, the second pad 370 may include a plurality of electrodes. For another example, the first pad 360 may include a plurality of electrodes.

According to an embodiment, the electronic device 301 (e.g., the processor 220) may use the first electrode 361 as a working electrode and the second electrode 362 as a counter electrode and a reference electrode to acquire first biometric information (e.g., fatigue level or blood glucose). For example, the electronic device 301 may control a voltage using an operational amplifier (op-amp) or a regulator.

According to an embodiment, the electronic device 301 may measure the fatigue level using the first electrode 361 and the second electrode 362. For example, if a voltage is applied between the first electrode 361 and the second electrode 362, lactic acid and oxygen contained in the sweat of the user may be decomposed into pyruvate and hydrogen peroxide by reacting with the catalyst applied to the first electrode 361. For example, the electronic device 201 may apply a voltage between the first electrode 361 and the second electrode 362, causing an oxidation reaction to hydrogen peroxide, which in turn, may generate electric charges between the first electrode 361 and the second electrode 362. According to an embodiment, the electronic device 301 may measure the amount of lactic acid by measuring the generated amount of electric charge. For example, a reaction layer containing lactate oxidase (LOx) for reaction with lactic acid may be coated on the surface of the first electrode 361. For example, the second electrode 362 may contain at least one of a metal (e.g., platinum, gold, silver, silver chloride, copper, or stainless steel), a conductive polymer (e.g., polyacetylene, polypyrrole, polythiophene, polyphenylene, polyphenylne, or PEDOT (poly(3, 4-ethylendioxythiophene)), or a transparent conductive material (indium tin oxide (ITO), aluminum-doped zinc oxide (AZO), tin(II) oxide (SnO), or fluorine doped tin oxide (FTO)).

According to an embodiment, the electronic device 301 may measure the fatigue level by applying a specified voltage (e.g., about 0.5 V or more and about 2 V or less) between the first electrode 361 and the second electrode 362 and measuring the amount of electric charge (e.g., current) through the second electrode 362. For example, the first electrode 361 may operate as a working electrode, and the second electrode 362 may operate as a counter electrode and/or a reference electrode.

According to an embodiment, in order to sense biometric information (e.g., first biometric information and/or second biometric information), the first pad 360 and/or the second pad 370 may include an electrolyte layer. For example, the electrolyte layer may include ions such as sodium ions (Na+) and chloride ions (Cl−). For example, the first electrode 361 and the second electrode 362 may constitute one electrical circuit including the electrolyte layer of the first pad 360.

According to an embodiment, the electronic device 301 may acquire the lactic acid concentration or the fatigue level corresponding to the amount of electric charge sensed through the first electrode 361 and the second electrode using an electric charge amount-lactic acid concentration or electric charge amount-fatigue level table stored in the memory 230. For example, the electronic device 301 may store the acquired lactic acid concentration or fatigue level in the memory 230 at a specified period (e.g., about 1 minute to about 10 minutes). For another example, the electronic device 301 may transmit the acquired lactic acid concentration or fatigue level to the external electronic device 202 at a specified period (e.g., about 1 minute to about 10 minutes).

According to an embodiment, the processor 220 may provide a warning to the user if the lactic acid concentration or fatigue level satisfies a first condition (e.g., if it is out of a specified range). For example, the processor 220 may provide a notification (e.g., a warning) using the display device 260 or using the external electronic device 202. For another example, the processor 220 may provide the notification using the configuration of the electronic device 201 or the external electronic device 202 for providing voice and/or tactile notification. The processor 220 may generate a warning by generating an interrupt.

According to various embodiments, the electronic device 301 may measure the blood glucose using the first electrode 361 and the second electrode 362. According to an embodiment, the first electrode 361 may include a reaction layer containing glucose oxidase (GOx) for selective reaction with glucose. For example, the reaction layer may be coated on the surface of at least a portion of the metal layer of the first electrode 361. According to an embodiment, the second electrode 362 may contain at least one of a metal (e.g., platinum, gold, silver, silver chloride, copper, or stainless steel), a conductive polymer (e.g., polyacetylene, polypyrrole, polythiophene, polyphenylene, polyphenylne, or PEDOT (poly(3, 4-ethylendioxythiophene)), or a transparent conductive material (indium tin oxide (ITO), aluminum-doped zinc oxide (AZO), tin(II) oxide (SnO), or fluorine doped tin oxide (FTO)). According to an embodiment, the electronic device 301 may measure the blood glucose by applying a specified voltage (e.g., about 0.5 V or more and about 2 V or less) between the first electrode 361 and the second electrode 362 and measuring the amount of electric charge (e.g., current) through the second electrode 362. For example, the first electrode 361 may operate as a working electrode, and the second electrode 362 may operate as a counter electrode and/or a reference electrode. According to an embodiment, in order to sense the first biometric information, the first pad 360 may include an electrolyte layer capable of electrically connecting the first electrode 361 and the second electrode 362. According to an embodiment, in order to sense the second biometric information, the first pad 360 and the second pad 370 may include the electrolyte layer. For example, the electrolyte layer may facilitate the sensing of the biometric information (e.g., first biometric information and/or second biometric information) by increasing the magnitude of the electrical signal (e.g., current and/or voltage) between electrodes (the first electrode 361, the second electrode 362, and/or the third electrode 371). For example, the electrolyte layer may include various ions (e.g., sodium ions and/or chloride ions). According to an embodiment, if the first electrode 361 and the second electrode 362 are used for blood glucose measurement, the first electrode 361 may have a positive oxidation potential and the second electrode 362 may have a negative reduction potential.

According to an embodiment, the electronic device 301 may acquire the glucose concentration or the blood glucose corresponding to the amount of electric charge sensed through the first electrode 361 and the second electrode by using the electric charge amount-glucose concentration or electric charge amount-blood glucose level table stored in the memory 230. For example, the electronic device 301 may store the acquired glucose concentration or blood glucose in the memory 230 at a specified period (e.g., about 1 minute to about 10 minutes). For another example, the electronic device 301 may transmit the acquired glucose concentration or blood glucose to the external electronic device 202 at a specified period (e.g., about 1 minute to about 10 minutes).

According to an embodiment, the processor 220 may provide a notification (e.g., warning) to the user if the glucose concentration or blood glucose satisfies a first condition (e.g., if it is out of a specified range).

According to an embodiment, the electronic device 301 may measure the second biometric information (e.g., electrocardiogram or GSR) using the second electrode 362 and the third electrode 371. The electronic device 301 may measure the second biometric information based on the voltage difference between the second electrode 362 and the third electrode 371. For example, the third electrode 371 may be formed of a metal (e.g., platinum, gold, silver, silver chloride, copper, or stainless steel), a conductive polymer (e.g., polyacetylene, polypyrrole, polythiophene, polyphenylene, polyphenylne, or PEDOT), or a transparent conductive material (ITO, AZO, SnO, or FTO). According to an embodiment, the third electrode 371 may be connected to a low pass filter (LPF), a high pass filter (HPF), and/or a band pass filter (BPF) for noise reduction.

According to an embodiment, the electronic device 301 may acquire electrocardiogram information based on the voltage difference between the second electrode 362 and the third electrode 371. For example, the processor 220 may provide a notification (e.g., warning) if the heart rate satisfies a specified condition (e.g., above or below a specified range).

According to various embodiments, the electronic device 301 may measure the GSR by applying a voltage between the second electrode 362 and the third electrode 371 and measuring the current between the second electrode 362 and the third electrode 371. For example, the electronic device 301 may measure the GSR by determining a resistance value based on the applied voltage and the measured current. For example, the processor 220 may determine the current stress state based on the measured GSR value, the amount of change in the GSR, and/or the change trend of the GSR. According to an embodiment, the processor 220 may provide a notification (warning) if the current stress state satisfies a specified condition (e.g., if it is out of a specified range).

In FIG. 3, the second pad 370 includes only the third electrode 371; however, according to various embodiments, the second pad 370 may further include one or more additional electrodes. For example, the second pad 370 may further include an additional electrode as a grip sensor for sensing attachment of the second pad 370. For another example, the second pad 370 may further include an additional electrode for measuring body temperature or skin humidity of the user. According to an embodiment, the third electrode 371 may be used to measure the electrocardiogram, and an additional electrode may be used to measure the GSR.

In the embodiments described above, the processor 220 may provide a notification (e.g., a warning), for example, using the display device 260 or using the external electronic device 202. For another example, the processor 220 may provide the notification using the configuration of the electronic device 201 or the external electronic device 202 for providing voice and/or tactile notification. The processor 220 may generate a warning by generating an interrupt.

Figure 4:
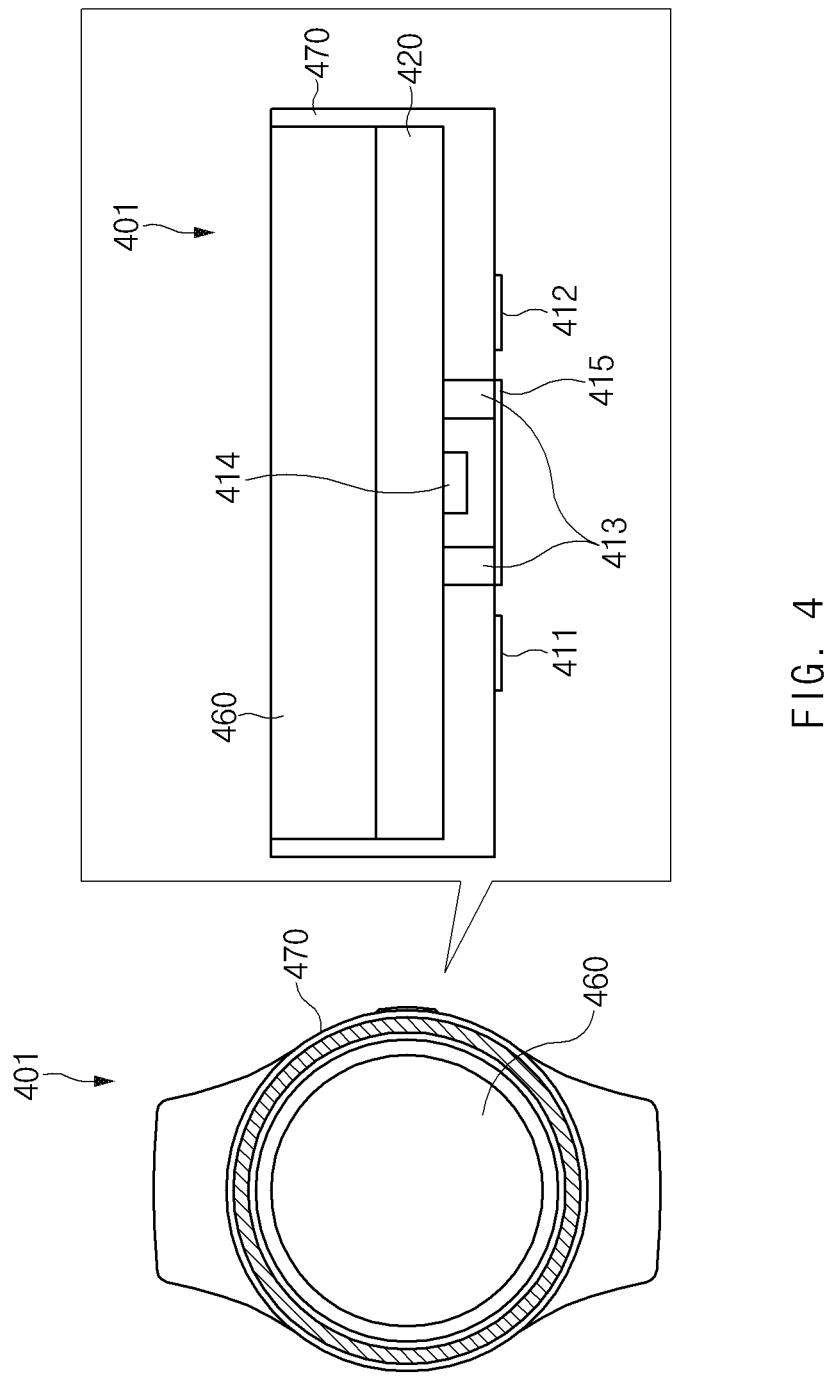
FIG. 4 is a diagram illustrating a configuration of the electronic device according to an embodiment.

FIG. 4 is a diagram illustrating a configuration of the electronic device according to an embodiment.

Referring to FIG. 4, according to various embodiments, an electronic device 401 (e.g., the electronic device 201) may be a wearable device (e.g., a smart watch). According to an embodiment, the electronic device 401 may include a display 460 exposed through a housing 470. For example, the display 460 may be controlled by a control unit 420, and sensor units 411, 412, 413, 414, and 415 may be positioned under the housing 470.

According to an embodiment, the electronic device 401 may include a photoplethysmography (PPG) sensor mounted under the housing 470. For example, the photoplethysmography (PPG) sensor may include an LED 413, an illuminance sensor 414, and a transparent window 415. The electronic device 401 may acquire heart rate information using the PPG sensor.

According to an embodiment, the electronic device 401 may measure the fatigue level using the first electrode 411 and the second electrode 412 positioned under the housing 470. For example, the electronic device 401 may apply a specified voltage (e.g., about 0.5 V to about 2 V) between the first electrode 411 and the second electrode 412, and may measure the fatigue level by measuring the amount of current between the first electrode 411 and the second electrode 412.

In FIG. 4, according to an embodiment, the electronic device 401 includes the first electrode 411 and the second electrode 412 for measuring the fatigue level. For example, a catalyst (e.g., LOx) for reaction with lactic acid may be applied or coated on the first electrode 411 and/or the second electrode 412.

According to an embodiment, the first electrode 411 and the second electrode 412 may be formed of a simple conductive material. For example, the first electrode 411 and the second electrode 412 may be formed of a material such as a metal, a conductive polymer, a conductive ceramic, and so on. The first electrode 411 and the second electrode 412 may be formed of the same material or different materials.

According to an embodiment, the catalyst layer coated on the surface of the electrode (e.g., the first electrode 411 and/or the second electrode 412) may be replaced. According to an embodiment, the electronic device 401 may replace the catalyst layer using a film-type electrode module. Hereinafter, referring to FIG. 5, the film-type electrode module will be described.

According to an embodiment, the electronic device 401 may correspond to the external electronic device 202 of FIG. 2, and the electronic device 301 of FIG. 3 may correspond to the electronic device 201 of FIG. 2.

Figure 5:
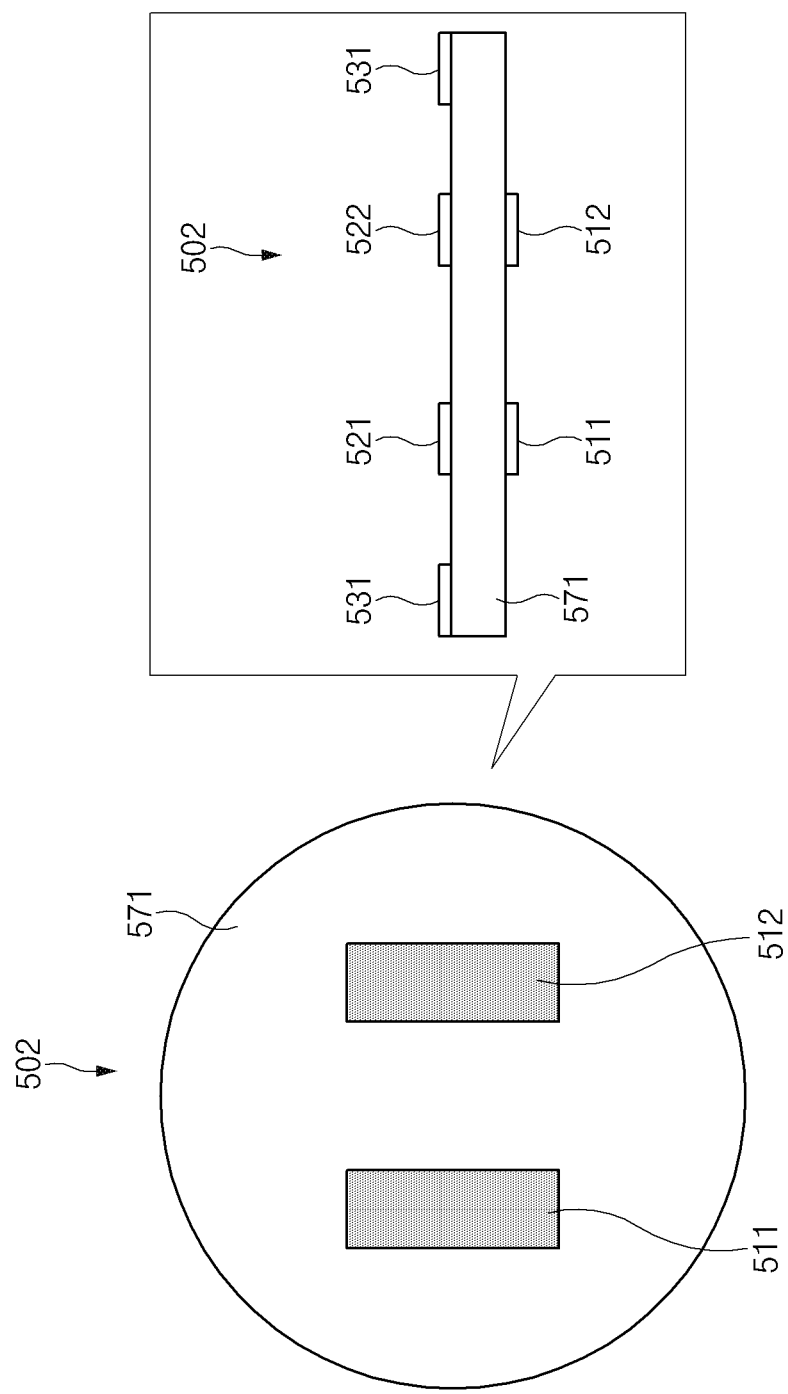
FIG. 5 is a diagram illustrating a structure of a film-type electrode module according to an embodiment.

FIG. 5 is a diagram illustrating a structure of a film-type electrode module 502 according to an embodiment.

According to various embodiments, the film-type electrode module 502 of FIG. 5 includes a third electrode 511 and a fourth electrode 512 positioned on the front surface of a transparent film 571 (e.g., a transparent polyethylene (PET) film, a polycarbonate (PC) film, an acrylate, and so on). According to an embodiment, an adhesive portion 531 (e.g., a silicone adhesive portion) may be positioned on the back surface of the transparent film 571. For example, the adhesive portion 531 may be formed along at least a portion of the circumference of the film-type electrode module 502. According to an embodiment, the adhesive portion 531 may be used to attach the film-type electrode module 502 to the lower portion of the housing 470 of the electronic device 401 in FIG. 4. According to an embodiment, a third electrode supporter 521 may electrically couple the first electrode 411 and the third electrode 511 of the electronic device (e.g., the electronic device 401 of FIG. 6). According to an embodiment, a fourth electrode supporter 522 may electrically couple the second electrode 412 and the fourth electrode 512 of the electronic device 401.

According to an embodiment, the third electrode 511 and the fourth electrode 512 may be formed of a conductive material (e.g., a metal, conductive polymer, or a conductive ceramic, or the like). A catalyst (e.g., LOx) capable of selectively reacting with lactic acid may be applied or coated on the third electrode 511 and/or the fourth electrode 512. For example, sensing sensitivity of biometric information may be maintained by replacing the film-type electrode module 502.

According to an embodiment, the film-type electrode module 502 is detachable to the electronic device 501. For example, in order to maintain the sensing sensitivity, the film-type electrode module 502 may be replaced at a certain period (e.g., about one week) or every predetermined use time.

According to an embodiment, the electronic device 401 may apply a specified voltage (e.g., about 0.5 V to about 2 V) between the third electrode 511 and the fourth electrode 512 using the first electrode 411 and the second electrode 412, and may measure the fatigue level by measuring the amount of current between the third electrode 511 and the fourth electrode 512.

According to various embodiments, the electronic device 401 may sense whether or not the film-type electrode module 502 is attached to the electronic device 401 or may acquire information about the attachment of the film-type electrode module 502 based on the user input. According to an embodiment, if the film-type electrode module 502 is attached, the electronic device 401 may acquire first biometric information (e.g., fatigue level) associated with the catalyst layer coated on the third electrode 511 and/or the fourth electrode 512. According to an embodiment, if the film-type electrode module 502 is not attached to the electronic device 401, the electronic device 401 may measure biometric information that does not require a catalyst. For example, the electronic device 401 may acquire heart rate information, GSR, and/or bioelectrical impedance analysis (BIA) using the first electrode 411 and the second electrode 412.

Figure 6:
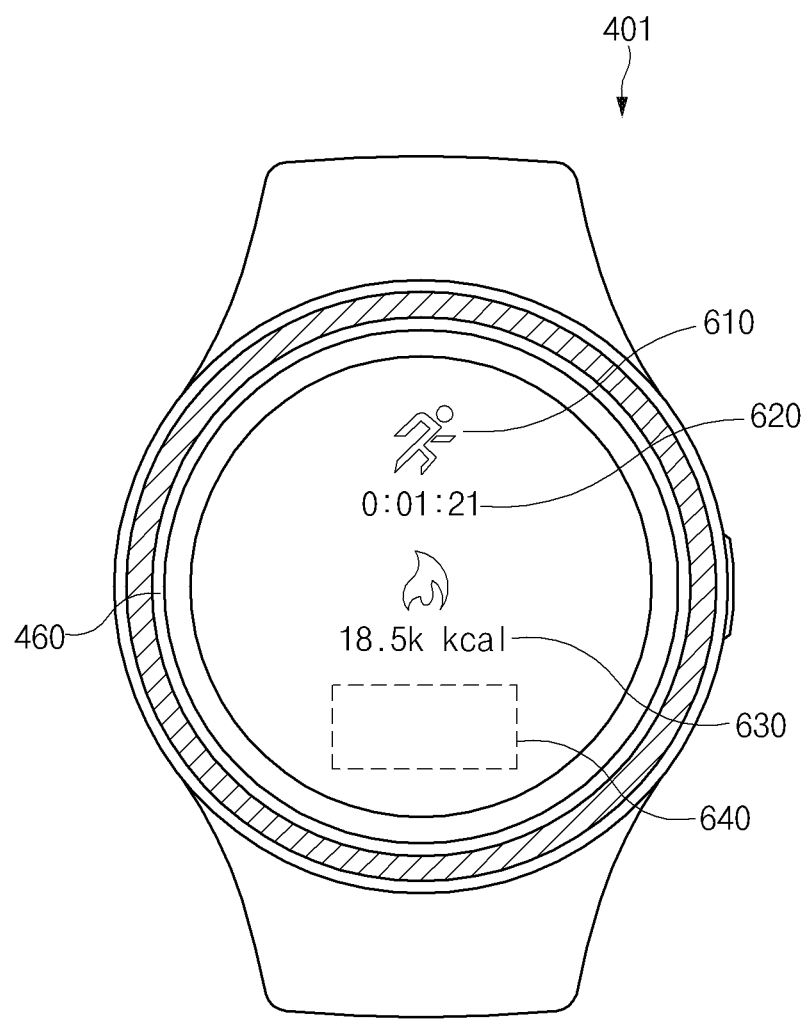
FIG. 6 is a diagram illustrating a user interface according to an embodiment.

FIG. 6 is a diagram illustrating a user interface according to an embodiment.

According to an embodiment, the electronic device 401 (e.g., the electronic device 201) may display information based on the measured biometric information on the display 460 (e.g., the display device 260). For example, the electronic device 401 may display information such as the exercise type, the exercise time, the amount of calories burned, and the like, on the display 460.

According to an embodiment, the electronic device 401 may determine the exercise type based at least on the movement of the user. In addition, the electronic device 401 may display acquired exercise type information 610. For another example, the exercise type information 610 may be set based on a user input.

According to an embodiment, the electronic device 401 may measure the exercise time based at least on the movement of the user. According to another embodiment, the electronic device 401 may measure the exercise time based on a user input. The electronic device 401 may display the measured exercise time information 620 on the display 460.

According to an embodiment, the electronic device 401 may display calories 630 burned on the display 460. For example, the electronic device 401 may acquire the calories 630 burned based at least on the determined exercise type and exercise time. According to an embodiment, the electronic device 401 may calculate the calories 630 burned using user information (e.g., gender, age, and/or body weight) stored in the memory (e.g., the memory 230 of FIG. 2) and a specified table. For example, the specified table may include information on calories burned per specified time according to body weight for each exercise type.

According to an embodiment, the electronic device 401 may display at least one information related to exercise on a first display region 640. For example, the electronic device 401 may display, on the first display region 640, at least one of an exercise warning for stopping exercise, an exercise notification for resuming exercise, or rest time information.

Figure 7:
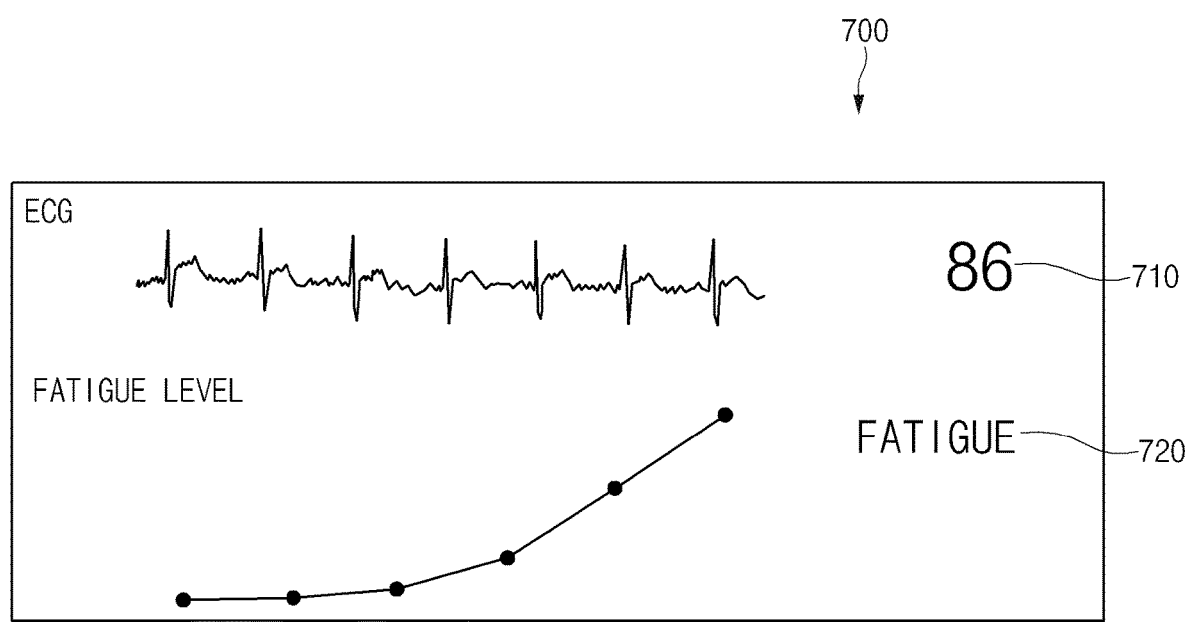
FIG. 7 is an example of a biometric information display.

FIG. 7 is an example of a biometric information display.

Referring to FIG. 7, an example of a user interface 700 indicating measured biometric information is illustrated. For example, the user interface 700 may include text (e.g., numbers or states) and/or graphic elements (e.g., graphs) displaying the measured biometric information.

According to an embodiment, the electronic device (e.g., the electronic device 201 of FIG. 2) may display the user interface (e.g., the user interface 700) indicating the measured biometric information on a display device (e.g., the display device 260). For example, the electronic device 201 may acquire raw data using a sensor module (e.g., the sensor module 276), and may display graphic elements (e.g., graphs) on the display device 260 using the raw data. The electronic device may determine the heart rate, the fatigue state (e.g., normal, fatigued, very fatigued, or the like), and/or a stress state (e.g., normal, stressful, or very stressful) based on the acquired raw data and may display the determined result on the display device. Referring to reference numeral 710 of FIG. 7, the electronic device 201 may display the heart rate of 86 per minute. Referring to reference numeral 720 of FIG. 7, the electronic device 201 may indicate that the user is currently fatigued, based on the currently measured lactic acid concentration.

According to an embodiment, the electronic device 201 may transmit the measured biometric information to an external electronic device (e.g., the external electronic device 202 of FIG. 2), thereby making it possible to display a user interface (e.g., the user interface 700) indicating the biometric information on the display of the external electronic device 202. For example, the electronic device 201 may acquire raw data using a sensor module (e.g., the sensor module 276) and may transmit the raw data to the external electronic device. For another example, the electronic device 201 may transmit, to the external electronic device 202, the raw data and/or information (e.g., the heart rate, the fatigue state, and/or the stress state) determined based on the raw data.

Figure 8:
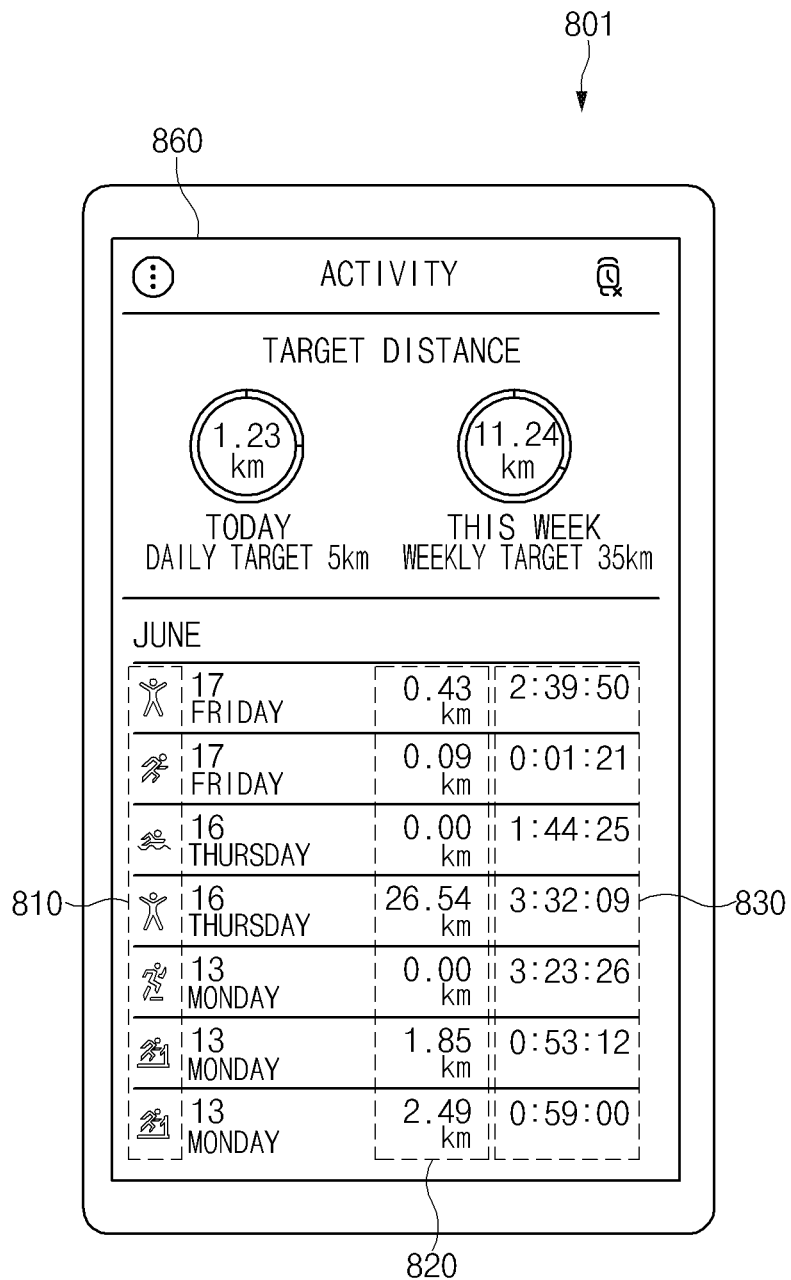
FIG. 8 is an example of an exercise information display.

FIG. 8 is an example of an exercise information display.

Referring to FIG. 8, the electronic device 801 may be an external electronic device (e.g., the external electronic device 202 of FIG. 2) that has received information from the electronic device 201 of FIG. 2.

According to an embodiment, the electronic device 801 may display one or more exercise information on a display 860. For example, the exercise information may include exercise type information 810, distance information 820, and exercise time information 830. According to an embodiment, the electronic device 801 may display, on the display 860, information received from a pad-type electronic device such as the electronic device 301 of FIG. 3 or a watch-type electronic device such as the electronic device 401 of FIG. 4 and information based at least on the information measured by the electronic device 801.

According to an embodiment, at least part of the information displayed on the display 860 of FIG. 8 may be displayed by the display device 260 of the electronic device 201. For example, the electronic device 201 may receive information from the external electronic device 202 (e.g., the electronic device 801) via the communication circuit 290. According to an embodiment, the electronic device 201 may display, on the display device 260, exercise information based on information received from the external electronic device 202 and/or information measured by the electronic device 201.

Figure 9:
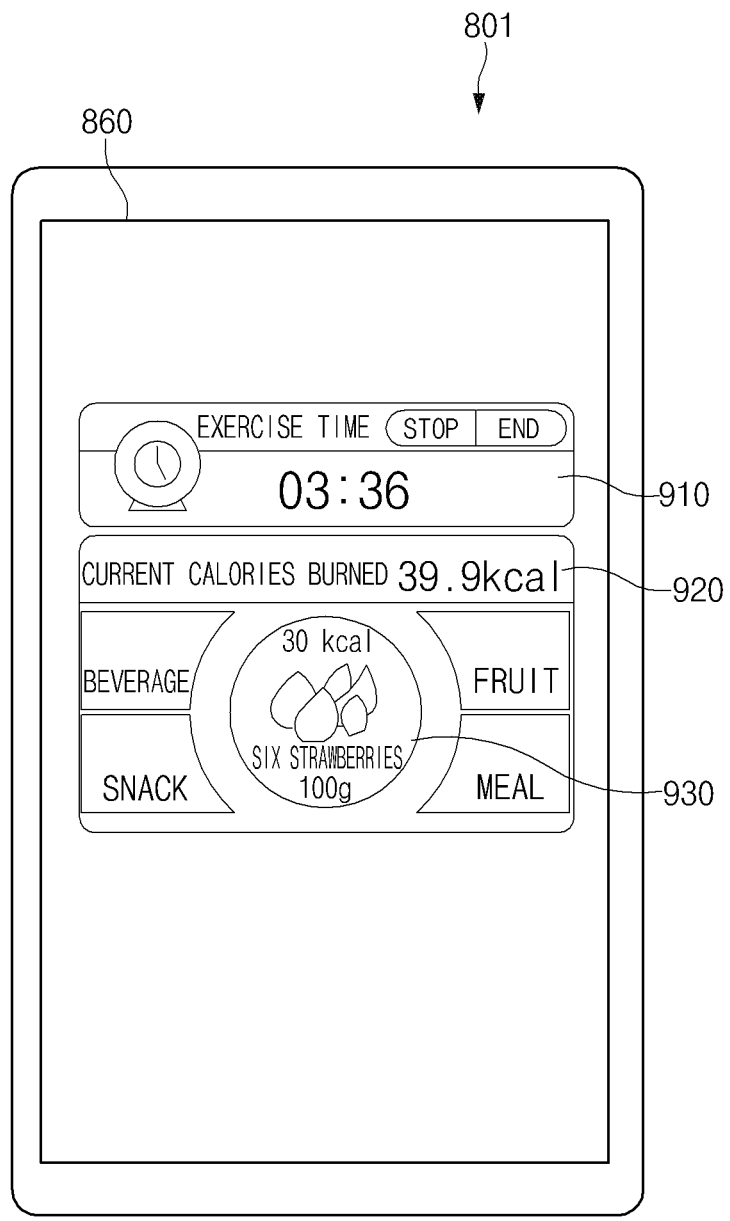
FIG. 9 is a diagram illustrating a user interface according to another embodiment.

FIG. 9 is a diagram illustrating a user interface according to another embodiment.

Referring to FIG. 9, the electronic device 801 may be an external electronic device (e.g., the external electronic device 202 of FIG. 2) that has received information from the electronic device 201 of FIG. 2.

According to an embodiment, the electronic device 801 may display, on the display 860, exercise time information 910, calories-burned information 920, and calorie intake information 930. According to an embodiment, the electronic device 801 may receive the exercise time information 910 and/or exercise type information from another electronic device (e.g., the electronic device 201 of FIG. 2), and may acquire the calories-burned information 920 based at least on the exercise time information 910 on and/or the exercise type information. According to an embodiment, the electronic device 801 may receive, from another electronic device, information or raw data for deriving the exercise time information 910 and/or the exercise type information.

According to an embodiment, the electronic device 801 may acquire the calorie intake information 930, based on a user input. For example, the electronic device 801 may acquire the calorie intake information 930 by receiving a user input for the amount and type of food or based on a photograph of food.

The user interface illustrated in FIG. 9 is exemplary, and the user interface herein is not limited thereto.

According to an embodiment, the user interface may include at least one of the calorie intake information according to food intake, information on exercise, or the calories-burned information. For example, the user interface may include an intake food input means capable of entering a meal type (e.g., breakfast, lunch, dinner or snack) and/or food type. For example, if the food type is selected based on an input of the user, the electronic device 801 may determine standard calories corresponding to the selected food. For example, if an amount of intake is input based on the input of the user, the electronic device 801 may acquire real calories based on the standard calories associated with the selected food.

According to an embodiment, the user interface may include an interface for receiving a user profile. For example, the user profile may include at least one of user identification information (e.g., name, gender, age, and/or date of birth), or physique conditions (e.g., height and/or weight).

According to an embodiment, the electronic device 801 may estimate basic metabolism based on the user profile. For example, the electronic device 801 may estimate the basic metabolism using a known method (e.g., estimation of a basic metabolic rate based on gender, age, and weight). For example, the electronic device 801 may calculate calories burned based on the basic metabolism and exercise information, and may display the result on the display 860.

According to an embodiment, the electronic device 801 may sense the start and end of the exercise, and may display exercise information (e.g., type and time) on the display 860. For example, the electronic device 801 may determine the start and end of the exercise by sensing movement or based on information received from another electronic device (e.g., the electronic device 201 of FIG. 2).

According to an embodiment, the electronic device 801 may display the amount of calories burned on the display 860 during exercise or at the time of finishing exercise. For example, the electronic device 801 may display the amount of calories burned based at least on information received from another electronic device (e.g., the electronic device 201 of FIG. 2). For another example, the electronic device 801 may display the amount of calories burned based on at least information received from the other electronic device 201 and/or a user profile stored in the electronic device 801.

According to an embodiment, the electronic device 801 may provide a recommended exercise type and exercise time for burning calories. For example, the electronic device 801 may provide a recommended exercise type and exercise time if the amount of calories burned is less than the amount of calories absorbed.

The examples of FIG. 9 have been mainly described for the electronic device 801; however, the same or similar method may be performed by the electronic device 201 of FIG. 2.

The user interface of FIG. 9 is exemplary, and the electronic device 401 may further provide health-related information in conjunction with other devices (e.g., a digital scale, and/or a blood glucose meter and so on).

Figure 10:
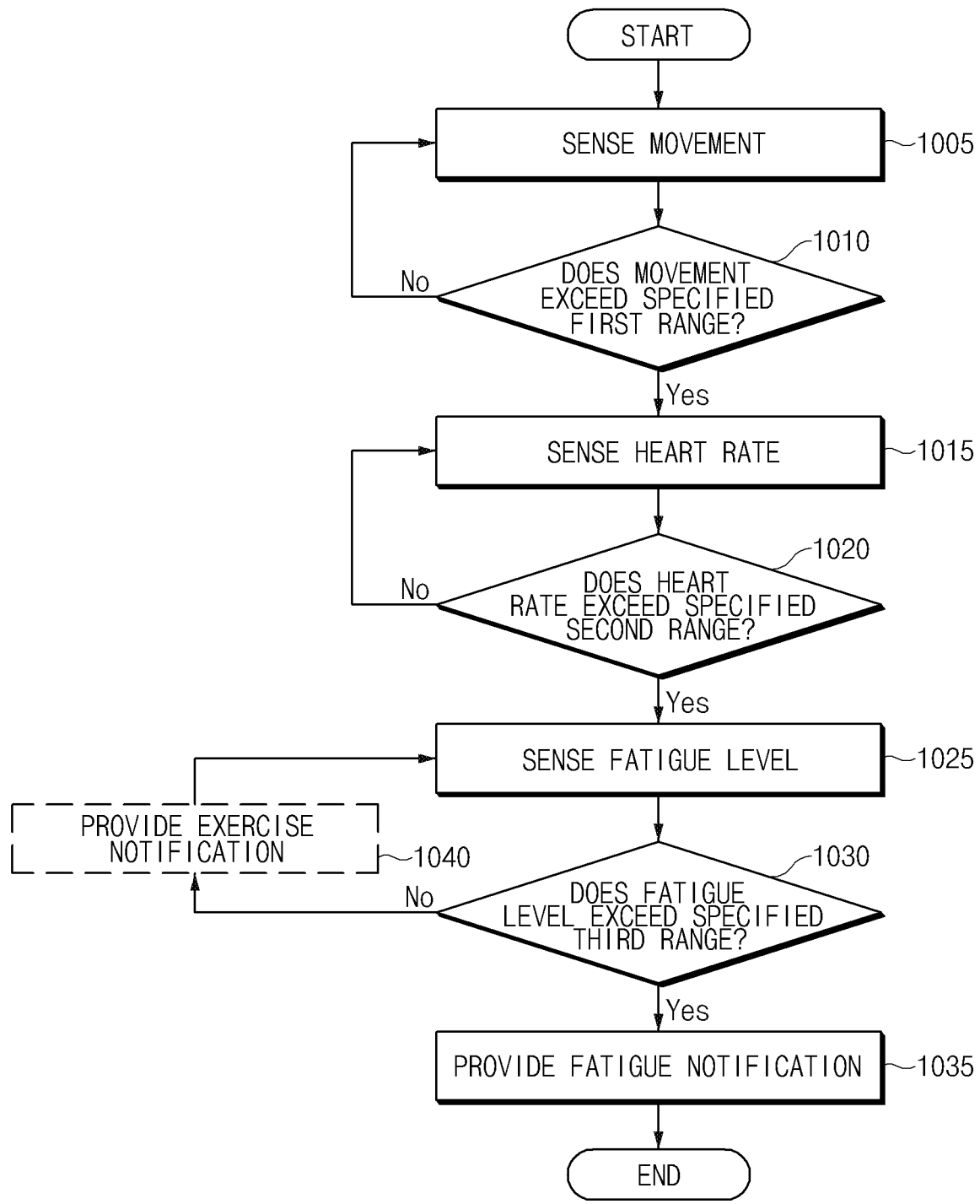
FIG. 10 is a flowchart of a fatigue notification method according to an embodiment.

FIG. 10 is a flowchart of a fatigue notification method according to an embodiment.

In operation 1005, according to various embodiments, the processor 220 of the electronic device (e.g., the electronic device 201 of FIG. 2) may sense the movement of the electronic device 201 using the sensor module 276. According to an embodiment, the processor 220 may sense the movement of the electronic device 201 by measuring physical movement. For example, the processor 220 may sense the movement of the electronic device 201 using the accelerometer and/or gyro sensor of the sensor module 276.

In operation 1010, according to various embodiments, the processor 220 may determine whether or not the sensed movement exceeds the specified first range (e.g., about 70% of the maximum heart rate corresponding to the age of the user). If the movement is equal to or less than the specified first range, the processor 220 may sense the movement again. For example, the processor 220 may periodically perform operation 1005.

In operation 1015, according to various embodiments, if the sensed movement exceeds the specified first range, the processor 220 may sense the heart rate. According to an embodiment, the processor 220 may sense the heart rate based on an electrical reaction. For example, the processor 220 may measure the heart rate based on the potential between a plurality of electrodes included in the sensor module 276. According to an embodiment, the processor 220 may measure the heart rate using the PPG sensor included in the sensor module 276.

In operation 1020, according to various embodiments, the processor 220 may determine whether or not the sensed heart rate exceeds the specified second range. If the heart rate is equal to or less than the specified second range, the processor 220 may continuously monitor the heart rate. For example, the processor 220 may periodically perform operation 1015.

According to various embodiments, instead of the operations 1015 and 1020, the processor 220 may sense biometric information of the external object (e.g., user). For example, the biometric information may include at least one of the heart rate, stress, blood pressure, or oxygen saturation. According to an embodiment, if the sensed biometric information exceeds the specified second range, the processor 220 may perform operation 1025, and if the sensed biometric information is less than the specified second range, the processor 220 may sense the biometric information of the external object again. According to an embodiment, the specified second range may be set based on age, gender, genetic characteristics (e.g., DNA), or activity information of the user.

In operation 1025, according to various embodiments, if the heart rate exceeds the specified second range, the processor 220 may measure the fatigue level using the sensor module 276. For example, the processor 220 may measure the fatigue level using two electrodes included in the sensor module. According to an embodiment, the processor 220 may measure the fatigue level based on the chemical reaction between a chemical material coated on the electrode and a fatigue measurement material (e.g., lactic acid).

In operation 1030, according to various embodiments, the processor 220 may determine whether or not the fatigue level exceeds the specified third range. If the fatigue level is equal to or less than the specified third range, the processor 220 may monitor the fatigue level. For example, the processor 220 may periodically identify the fatigue level. In addition, in operation 1040, the processor 220 may provide an exercise notification recommending an exercise to the user. For example, the processor 220 may transmit a message for providing a notification to the external electronic device 202 using the communication circuit 260.

In operation 1035, according to various embodiments, if the fatigue level exceeds the specified third range, the processor 220 may provide a fatigue notification. For example, the processor 220 may provide the fatigue notification using the display device 260 or the external electronic device 202. The fatigue notification may include a warning to stop exercising.

Figure 11:
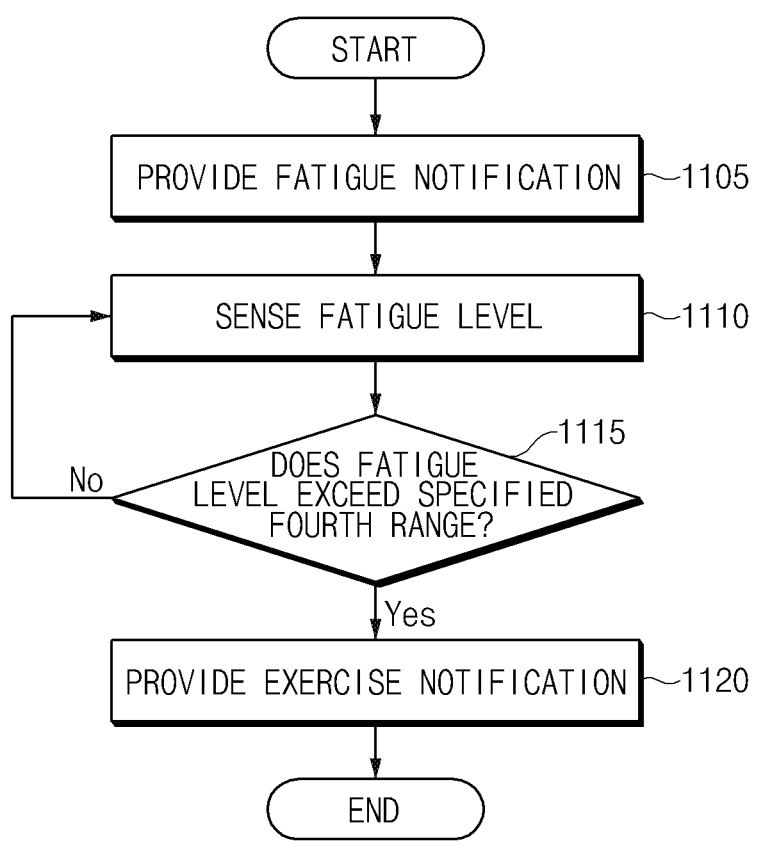
FIG. 11 is a flowchart of an exercise notification method according to an embodiment.

FIG. 11 is a flowchart of an exercise notification method according to an embodiment.

In FIG. 11, operation 1105 is the same as operation 1035 of FIG. 10. For example, operation 1110 may be performed subsequent to operation 1035 of FIG. 10.

In operation 1110, according to various embodiments, the processor 220 of the electronic device (e.g., the electronic device 201 of FIG. 2) may sense the fatigue level. According to an embodiment, the processor 220 may sense the fatigue level using the fatigue sensor of the sensor module 276. According to an embodiment, the processor 220 may sense the fatigue level and the heart rate. For example, the processor 220 may sense the heart rate using the PPG sensor and/or ECG sensor of the sensor module 276.

In operation 1115, according to various embodiments, the processor 220 may determine whether or not the fatigue level is equal to or less than the specified fourth range. If the fatigue level exceeds the specified fourth range, the processor 220 may continuously monitor the fatigue level. For example, the processor 220 may periodically sense the fatigue level (or fatigue level and heart rate).

In operation 1120, according to various embodiments, if the fatigue level is less than or equal to the specified fourth range, the processor 220 may provide an exercise notification for recommending exercise. For example, the processor 220 may provide the exercise notification using the display device 260 or the external electronic device 202. For another example, if the fatigue level is less than the specified fourth range and the heart rate is less than a specified fifth range, the processor 220 may provide the exercise notification.

Figure 12:
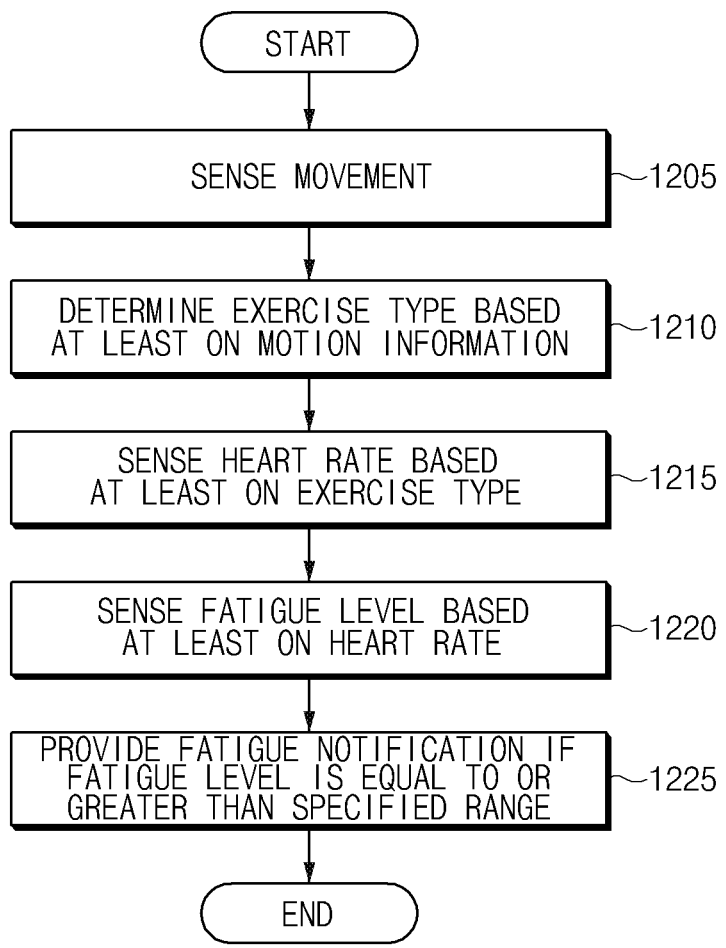
FIG. 12 is a flowchart of a fatigue notification method according to an embodiment.

FIG. 12 is a flowchart of a fatigue notification method according to an embodiment.

Operations described below may be referred to by those described above with reference to FIG. 11. For convenience of description, the same description is omitted.

In operation 1205, according to various embodiments, the processor 220 of the electronic device (e.g., the electronic device 201 of FIG. 2) senses the movement of the electronic device 201. The specific details may be referred to by those as described above with reference to operation 1005.

In operation 1210, according to various embodiments, the processor 220 may determine the exercise type based at least on motion information. According to an embodiment, the processor 220 may acquire the motion information using at least one of the acceleration sensor, the gyro sensor, or the air pressure sensor, of the sensor module 276. According to an embodiment, the processor 220 may determine the exercise type based at least on the motion information based on a specified condition. For example, the processor 220 may determine the exercise type if the motion information exceeding a specified size and/or a specified time is sensed. For example, the processor 220 may determine that the exercise type is "walking" if the movement corresponding to "walking" continues for a specified time (e.g., about 10 minutes) or more. According to an embodiment, the processor 220 may determine a significant movement (e.g., the exercise type) based on the motion information.

In operation 1215, according to various embodiments, the processor 220 may sense a heart rate based at least on the exercise type. For example, the processor 220 may sense the heart rate based on a significant movement. According to an embodiment, when the exercise type is determined, the processor 220 may sense the heart rate. For example, the processor 220 may sense the heart rate if a movement (e.g., a significant movement) corresponding to the exercise type is sensed to be equal to or greater than a specified first range (e.g., specified time and/or size). According to an embodiment, the processor 220 may sense the heart rate using at least one of the PPG sensor or the ECG sensor of the sensor module 276.

In operation 1220, according to various embodiments, the processor 220 may sense a fatigue level based on at least the heart rate. For example, the processor 220 may sense the fatigue level if the heart rate is greater than or equal to the specified second range. According to an embodiment, the processor 220 may sense the fatigue level using the fatigue sensor of the sensor module 276.

In operation 1225, according to various embodiments, the processor 220 may provide a fatigue notification if the fatigue level is greater than or equal to a specified range. According to an embodiment, the processor 220 may transmit information corresponding to the fatigue notification to the external electronic device 202 using the communication circuit 290. For example, the processor 220 may provide the fatigue notification via the external electronic device 202. According to an embodiment, the processor 220 may provide the fatigue notification using the display device 260.

The operations of the electronic device described above with reference to FIGS. 10 to 12 are exemplary, and the operations described above may be combined with the configurations and operations of the electronic device described above with reference to FIGS. 1 to 9.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance.

According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smartphones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. A wearable electronic device configured to be worn on a user comprising:
   a display;
   an accelerometer;
   a heart rate sensor;
   a fatigue sensor; and
   a processor,
   wherein the processor is configured to:
      sense movement of the wearable electronic device using the accelerometer;
      when the sensed movement exceeds a threshold movement, sense a heart rate of the user using the heart rate sensor;
      when the sensed heart rate exceeds a threshold heart rate, sense fatigue of the user based on electric current detected by using the fatigue sensor; and
      when the sensed fatigue exceeds a first threshold fatigue, output a fatigue notification on the display, the fatigue notification indicating a fatigue state.

2. The wearable electronic device of claim 1, wherein the processor is further configured to:
   continue monitoring the movement of the wearable device using the accelerometer when the sensed movement is equal to or less than the threshold heart rate.

3. The wearable electronic device of claim 2, wherein the threshold heart rate is set based on at least one of an age, gender, genetic characteristics or activity information of the user.

4. The wearable electronic device of claim 2, wherein the processor is further configured to:
   determine an exercise type and an exercise time based on the sensed movement of the wearable electronic device.

5. The wearable electronic device of claim 4, wherein the processor is further configured to:
   calculate calories burned based on the determined exercise type and the determined exercise time; and
   output the calculated calories burned on the display.

6. The wearable electronic device of claim 1, wherein the fatigue sensor is configured to, when the sensed heart rate exceeds the threshold heart rate:

apply a specified voltage between a first electrode of the fatigue sensor and a second electrode of the fatigue sensor, the second electrode including a catalyst layer for reaction with lactic acid;

measure an amount of current between the first electrode and the second electrode; and measure lactic acid concentration based on the amount of current.

7. The wearable electronic device of claim 1, wherein the heart rate sensor includes at least one of a photoplethysmography (PPG) sensor or an electrocardiography (ECG) sensor.

8. A method of providing a fatigue notification by a wearable electronic device, the method comprising:

sensing movement of the wearable electronic device using an accelerometer of the wearable electronic device;

when the sensed movement exceeds a threshold movement, sensing a heart rate of a user of the wearable electronic device using a heart rate sensor of the wearable electronic device;

when the sensed heart rate exceeds a threshold heart rate, sensing fatigue of the user based on electric current detected by using a fatigue sensor of the wearable electronic device; and when the sensed fatigue exceeds a first threshold fatigue, outputting a fatigue notification on a display of the wearable electronic device, the fatigue notification indicating a fatigue state.

9. The method of providing a fatigue notification of claim 8, wherein the threshold heart rate is set based on at least one of an age, gender, genetic characteristics, or activity information of the user.

10. The method of providing a fatigue notification of claim 8, further comprising:

determining an exercise type and an exercise time based on the sensed movement of the wearable electronic device.

11. The method of providing a fatigue notification of claim 10, further comprising:

calculating calories burned based on the determined exercise type and the determined exercise time; and outputting the calculated calories burned on the display.

* * * * *